United States Patent
Couzy et al.

(10) Patent No.: US 7,479,286 B2
(45) Date of Patent: Jan. 20, 2009

(54) DIETARY LIPIDS FOR IMPROVING SKIN AND COAT OF PETS

(75) Inventors: François Couzy, La Croix/Lutry (CH); Catherine Boissin-Delaporte, Echenevex (FR)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 10/339,349

(22) Filed: Jan. 10, 2003

(65) Prior Publication Data

US 2003/0152664 A1 Aug. 14, 2003

Related U.S. Application Data

(63) Continuation of application No. PCT/EP01/06937, filed on Jun. 18, 2001.

(30) Foreign Application Priority Data

Jul. 14, 2000 (EP) ................... 00115272

(51) Int. Cl.
*A23K 1/18* (2006.01)
(52) U.S. Cl. .................... 424/442; 426/2; 426/53; 426/54; 426/321; 426/325; 426/632; 426/635; 426/805; 514/558; 514/560
(58) Field of Classification Search ................. 424/442; 426/2, 53, 54, 326, 335, 532, 635, 805; 574/558, 574/560

See application file for complete search history.

(56) References Cited

U.S. PATENT DOCUMENTS

| | | | | | |
|---|---|---|---|---|---|
| 4,002,775 | A | * | 1/1977 | Kabara | 424/312 |
| 4,208,429 | A | | 6/1980 | Fraser | 424/312 |
| 5,776,913 | A | * | 7/1998 | Ogilvie et al. | 514/57 |
| 5,965,153 | A | | 10/1999 | Allen | 424/442 |
| 6,077,867 | A | * | 6/2000 | Pageat | 514/558 |

FOREIGN PATENT DOCUMENTS

| | | |
|---|---|---|
| WO | WO 98/16104 | 4/1998 |
| WO | WO 99/66804 | 12/1999 |
| WO | WO99/66804 | * 12/1999 |

OTHER PUBLICATIONS

Lechowski et al., XP 000971544, "The effect of the addition of oil preparation with increased content of n-3 fatty acids on serum lipid profile and clinical condition of cats with *Miliary dermatitis*", Journal of Veterinary Medicine, Series A-Xentralblatt Fuer Veterinaermedizin, Reihe A. vol. 45, pp. 417-424 (1998).

Ulmanen et al., XP000971396, "Effect of diet on skin fatty acid profile in mink", ACTA Agricultuare Scandinavica, Stolkholm SE ISSN:0001-5121, vol. 14, pp. 171-178 (1991).

* cited by examiner

*Primary Examiner*—Neil Levy
(74) *Attorney, Agent, or Firm*—Bell, Boyd & Lloyd LLP

(57) ABSTRACT

A source of dietary lipids containing anti-microbial fatty acids is added to a food composition intended for improving or maintaining the skin health and/or coat quality in a pet by preventing or regulating the growth of skin pathogens and of microflora responsible for the generation of body surface and coat odors.

1 Claim, 1 Drawing Sheet

DIETARY LIPIDS FOR IMPROVING SKIN AND COAT OF PETS

CROSS-REFERENCE TO RELATED APPLICATIONS

Figure 1:
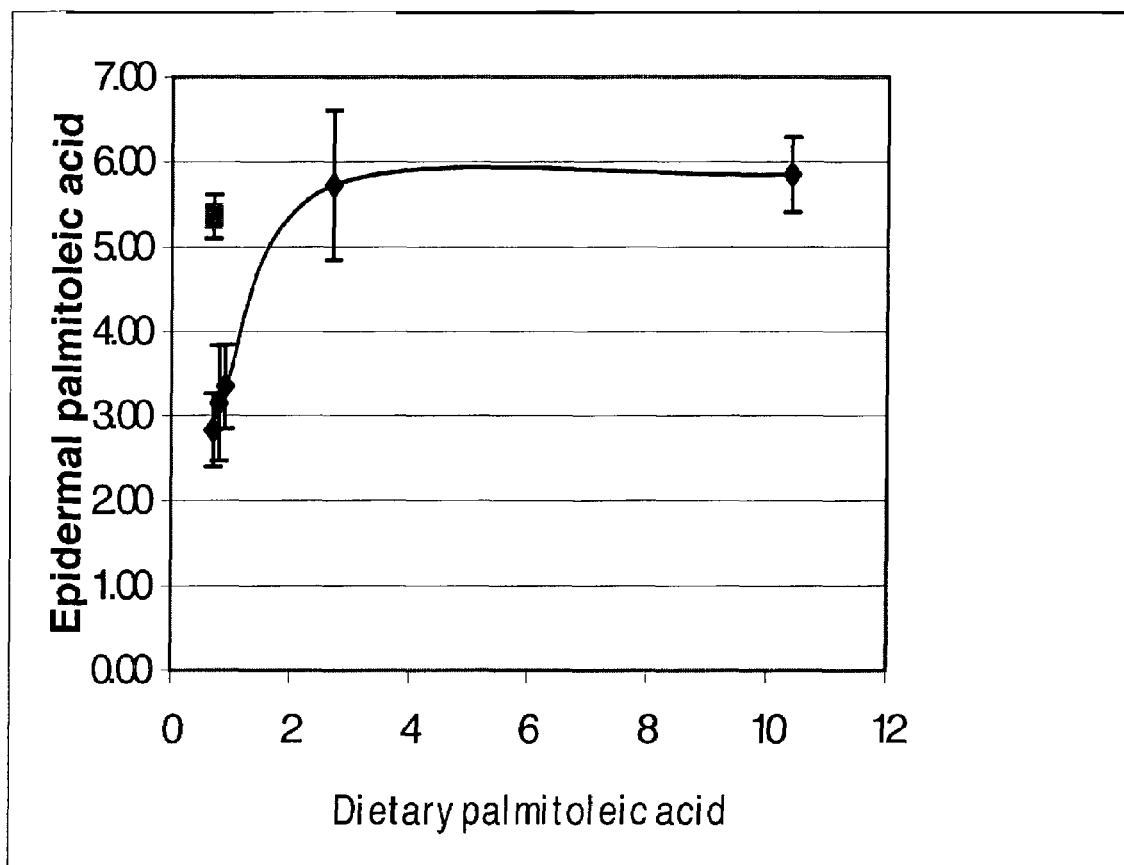

This application is a continuation of the US national phase designation of International application PCT/EP01/06937 filed Jun. 18, 2001, the content of which is expressly incorporated herein by reference thereto.

BACKGROUND OF THE INVENTION

This invention relates to the use of a source of dietary lipids for the preparation of a food composition intended for improving or maintaining the skin health and/or coat quality in a pet by regulating the level of the anti-microbial fatty acids in the epidermis of animal. The invention also relates to a method for improving skin health and/or coat quality in a pet, and the petfood formulation thereon.

Skin is the outer boundary of the body, and plays a key role as a barrier between a living organism and the environment. One of the most important functions of the skin is to retain water and hydrosoluble compounds from leaving or entering the body. Impaired barrier function of the skin may lead to e.g., increased susceptibility to skin infections, inflammation, itching.

Most of the barrier function of the skin is provided by the outer layer of the epidermis, the stratum corneum. It consists mainly of layers of keratinocytes which die as they progress towards the surface and are shed. The stratum corneum contains lipids which help maintain the cohesion between the keratinocytes, thus ensuring the waterproofing of the epidermis.

There are several situations when the barrier function of the skin is adequate under normal conditions, but becomes insufficient due to changes in physiological, environmental, or pathological conditions. The skin generally adapts to those conditions by increasing the synthesis of skin lipids: triglycerides, cholesterol and cholesterol esters, ceramides (Grubauer et al, 1987, Journal of Lipid Research 1987; 28 (6): 746-752). This process allows the skin to reach an adequate level of protection after about 48 hours.

Nutrition may impact skin barrier function. The international patent application WO 9856263 discloses the combination of linoleic acid and zinc for the improvement of skin quality and coat condition in pets, for example.

Another aspect by which nutrition may impact the skin is through fatty acids might inhibit the development of inflammatory reactions on the skin, e.g., the fatty acid a-linolenic (Vaughn DM et al, 1994, *Vet. Dermatol.* 5: 163-173).

It is known that skin lipids, and more specifically, free fatty acids can be anti-microbial to Gram-positive pathogenic bacteria (Bibel D. J. et al., 1989, J. Invest. Dermatol, 92, 632-638). In particular, palmitoleic and lauric acids are known for their anti-microbial activity against common skin pathogens from in vitro studies. Indeed, lauric acid, palmitoleic acid or linoleic acid were shown inhibitory in vitro against several skin pathogens such as Pneumococci, Streptococcus, Corynebacteria, Micrococci, Candida, *Staphylococcus aureus* (Kabara et al., 1972, *Antimicro. Agents and Chemo.*, 2, 23-28 and, 1978, *J. Soc. Cosmet. Chem.*, 29, 733-741).

However, there is no data on the effect of nutritionally induced increased concentration of such fatty acids for an increased protection against pathogens growth, i.e. increasing the level of antimicrobial fatty acids in the epidermis or the skin by nutrition.

SUMMARY OF THE INVENTION

Accordingly, in one aspect, this invention relates to the use of a source of dietary lipids for the preparation of a food composition intended for improving or maintaining skin health and/or coat quality in a pet by preventing or regulating the growth of skin pathogens and of microflora-generated odors.

It is surprisingly found that some dietary lipids have the ability to modulate the composition of skin lipids and epidermal fatty acids content, particularly by inducing an increase of bioavailable anti-microbial fatty acids in the epidermis of animals, for example, and hence improve skin health and/or coat quality of the pet.

Preferably, the source of dietary lipids according to the present invention may improve the level of the anti-microbial fatty acids lauric acid and palmitoleic acid in the epidermis of animals. These fatty acids are active against skin pathogens such as *Staphylococcus aureus, Staphylococcus intermedius* or *Malassezia pachydermatis,* for example.

The dietary fatty acids may be from vegetable origin. They are preferably in the form of a mix of edible oils and fats or food containing those, comprising at least dietary palmitoleic acid, and more preferably in combination with other dietary fatty acids such as lauric acid, linoleic acid, alpha- or gamma-linolenic acid.

In a preferred embodiment, the dietary fatty acids are used in an amount sufficient to achieve a level of at least 5% of anti-microbial fatty acids in the epidermis of animals, and more preferably of at least 5% of epidermal palmitoleic acid.

Accordingly, the fat source of dietary fatty acids may contain dietary palmitoleic acid in an amount of at least 2.5% by weight on a dry weight basis of total fatty acids, and preferably from about 3 to 10% of total dietary fatty acids.

The source of dietary fatty acids may also consist of a mix of at least dietary palmitoleic and lauric acids. Dietary palmitoleic acid may thus be used in an amount of at least 0.2% in combination with at least about 10% of dietary lauric acid by weight on a dry weight basis of total fatty acids. A synergistic effect of this mix on epidermal palmitoleic acid has been shown in example 2. This mix may also increase the epidermal lauric acid up to about 3.0% of epidermal fatty acids.

In a further aspect, this invention provides a method for improving skin health and/or coat quality in a pet, including the steps of feeding it a petfood formulation comprising at least a source of dietary lipids having the ability to modulate the composition of skin lipids and epidermal anti-microbial fatty acid content.

The invention further provides a method for reducing body surface odor and/or coat odors of a pet, including the step of feeding it a petfood formulation comprising at least a source of dietary lipids having the ability to modulate the content of anti-microbial fatty acids in the epidermis.

The source of dietary lipids is preferably as described above.

This method may improve or maintain skin health and/or coat quality in a pet by preventing the growth of skin pathogens and of microflora responsible for the generation of body surface and coat odors.

In another aspect, the invention provides a pet food formulation comprising a source of dietary lipids selected for their ability to modulate the composition of skin lipids and epidermal anti-microbial fatty acids content.

The petfood formulation is preferably a complete and nutritionally balanced pet food. Alternatively, it may be a dietary supplement or an adjunct for addition to a main meal or snack.

The petfood formulation thus comprises a lipid agent capable of inhibiting the growth of skin pathogens and of microflora responsible for the generation of body surface and coat odors.

In yet an embodiment, the pet food formulation may also contain linoleic, α- and γ-linolenic acids, in amount sufficient to improve or maintain skin health.

BRIEF DESCRIPTION OF THE DRAWING FIGURE

FIG. 1 is an illustration of the relationship between dietary and epidermal palmitoleic acid in nude mice fed diets with various oil blends (both expressed as % of fatty acids). Each point is an average value (with n=10). Mean±SD, with n=10.

DETAILED DESCRIPTION OF THE PREFERRED EMBODIMENTS

The present invention provides for the use of a source of dietary lipids for the preparation of a food composition intended for improving or maintaining the skin health and/or coat quality in a pet by preventing or regulating the growth of skin pathogens and of microflora-generated odors.

It is surprisingly found that certain dietary lipids have the ability to induce an increase of bioavailable anti-microbial fatty acids in the epidermis of animals, while also maintaining an adequate barrier function of the skin. In general, these are active fatty acids having from C:10 to C:18. These anti-microbial fatty acids in the epidermis preferably are palmitoleic and lauric acids. At the same time, the level in the epidermis of fatty acids with a role in skin barrier function and permeability (linoleic acid), as well as those with anti-inflammatory (α-linolenic and γ-linolenic acid) activities, may also be increased.

The source of dietary lipids according to the present invention may particularly improve or modulate the level of the anti-microbial fatty acids lauric acid and palmitoleic acid in the epidermis and in epidermal secretions of animals. These fatty acids are active against skin pathogens such as *Staphylococcus aureus, Staphylococcus intermedius* or *Malassezia pachydermatis*, for example.

The dietary lipids are from any suitable source and preferably from vegetable origin. The source of dietary lipids may be a mix of edible oils and fats or food containing those, comprising at least dietary fatty acids such as palmitoleic acid, and more preferably in combination with other dietary fatty acids such as lauric acid, linoleic acid, α- or γlinolenic acid.

In a preferred embodiment, the dietary fatty acids are used in an amount sufficient to achieve a level of at least 5% of anti-microbial fatty acids in the epidermis of animals, and more preferably of at least about 5% of epidermal palmitoleic acid.

Accordingly, the source of dietary fatty acids may contain at least dietary palmitoleic acid in an amount of at least 2.5% by weight on a dry weight basis of total dietary fatty acids, and preferably from about 3% to 10% of total dietary fatty acids.

The source of dietary fatty acids may also consist of a mix of at least dietary palmitoleic and lauric acids. When expressed as a percent of the final product, dietary palmitoleic acid may thus be used in an amount of at least 0.02%, in combination with at least about 1.0% of dietary lauric acid. The mix may also contain at least 1.0% linoleic acid. A synergistic effect of this mix on epidermal palmitoleic acid has been shown in example 2. This mix may also increase the epidermal lauric acid up to about 3.0% of epidermal fatty acids.

The fatty acid composition may also be further adjusted so as to provide an optimal (n-6)/(n-3) ratio, of about from 7 to 15.

Dietary palmitoleic acid can be sourced from tallow (mutton, beef), poultry (e.g. chicken, duck) but also from a suitable vegetable source. It can also be sourced from microbial cultures, for example, yeasts or yeast lipids.

Dietary lauric acid can be sourced from coconut oil, babassu oil, cohune oil, murumuru tallow, palm kernel oil or tucum oil, for example.

The oral administration of the dietary lipids according to the invention or of a food containing those will result in an increased level of the antimicrobial fatty acids lauric and palmitoleic acid in the epidermis. This will increase the capacity of the skin to resist to infestation by skin pathogens, e.g. Staphylococcus aureus, Staphylococcus intermedius, Malassezia pachydermatis.

In a further aspect, this invention provides a method for maintaining or improving skin health and/or coat quality in a pet, including the steps of feeding it a petfood formulation comprising at least a source of dietary lipids having the ability to modulate the composition of skin lipids and epidermal fatty acids content.

The method may include inhibiting or preventing the growth of skin pathogens and of microflora responsible for the generation of body surface and coat odors, for example.

The source of dietary lipids is selected to provide the above described benefits.

The amount of the pet food formulation to be consumed by the pet to obtain a beneficial effect will depend upon the size of the pet, the type of pet, and age of the pet. However a concentration in the pet food of about 0.4% palmitoleic acid by weight on a dry weight basis, or of about 0.10 g/100 kcal more preferably used. Also, a concentration in the pet food of about 0.05% palmitoleic acid by weight on a dry weight basis in combination with 1.0% dietary lauric acid is more preferably used.

Furthermore, the invention provides a pet food formulation comprising a source of dietary lipids selected for their ability to modulate the composition of skin lipids and epidermal anti-microbial fatty acids content.

Preferably, the source of dietary lipids is capable of preventing or at least inhibiting the growth of skin pathogens and of microflora responsible for the generation of body surface and coat odors.

The petfood formulation is preferably a complete and nutritionally balanced pet food. It can also be a dietary supplement for pets or in the form of a pharmaceutical composition.

The nutritionally complete pet food formulation according to the invention may be in any suitable form, for example a powder, a dried kibble, or pellet or other dried form, extruded form, semi-moist or wet form, such as a chunk or loaf or pudding. It may be chilled or provided as a shelf stable product.

This pet food may be produced by conventional methods, it may include any one or more of a starch source, a protein source and lipid source, the last one being composed partially or in totality of the fat mix described above.

Suitable starch sources are, for example, grains and legumes such as corn, rice, wheat, barley, oats, soy, and mixtures of these.

Suitable protein sources may be selected from any suitable animal or vegetable protein source; for example meat and meat meal, poultry meal, fish meal, soy protein concentrates, milk proteins, gluten, and the like. For elderly animals, it is preferred for the protein source to contain a high quality protein.

Suitable lipid sources include meats, animal fats and vegetable fats, as well as oleaginous grains and beans.

The choice of the starch, protein and lipid sources will be largely determined by the nutritional needs of the animal, palatability considerations, and the type of product produced. For elderly pets, the pet food preferably contains proportionally less fat than pet foods for younger pets. Further, the starch sources may include one or more of rice, barley, wheat and corn.

The pet food may optionally also contain a prebiotic, a probiotic microorganism or another active agent, for example a long chain fatty acid. The amount of prebiotic in the pet food is preferably less than 10% by weight. For example, the prebiotic may comprise about 0.1% to about 5% by weight of the pet food. For pet foods which use chicory as the source of the prebiotic, the chicory may be included to comprise about 0.5% to about 10% by weight of the feed mixture; more preferably about 1% to about 5% by weight.

If a probiotic microorganism is used, the pet food preferably contains about $10^4$ to about $10^{10}$ cells of the probiotic microorganism per gram of the pet food; more preferably about $10^6$ to about $10^8$ cells of the probiotic microorganism per gram. The pet food may contain about 0.5% to about 20% by weight of the mixture of the probiotic microorganism; preferably about 1% to about 6% by weight; for example about 3% to about 6% by weight.

Suitable long chain fatty acids include linoleic acid, alpha-linolenic acid, gamma linolenic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Safflower oils, sunflower oils, corn oils and soy bean oils are suitable sources of linoleic acid.

If necessary, the pet food is supplemented with minerals and vitamins so that they are nutritionally complete. Further, various other ingredients, for example, sugar, salt, spices, seasonings, flavoring agents, and the like may also be incorporated into the pet food as desired.

For dried pet food a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569; the disclosure of which is incorporated by reference. If a probiotic microorganism is used, the organism is preferably coated onto or filled into the dried pet food. A suitable process is described in European patent application No 0862863; the disclosure of which is incorporated by reference.

For wet food, the processes described in U.S. Pat. Nos. 4,781,939 and 5,132,137 may be used to produce simulated meat products. The disclosures of these patents are incorporated by reference. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

The amount of the pet food to be consumed by the pet to obtain a beneficial effect will depend upon the size or the pet, the type of pet, and age of the pet. However a concentration in the pet food of 0.4% palmitoleic acid by weight on a dry weight basis, or of 0.1 g/100 kcal is more preferably used. Also, a concentration in the pet food of about 0.05% palmitoleic acid by weight on a dry weight basis in combination with 1.0% dietary lauric acid is more preferably used.

The effect of the dietary fatty acids was evaluated on epidermal fatty acids and skin bather function in vivo trials. The level of anti-microbial fatty acids in the epidermis can be manipulated by diet.

In a last aspect, the pet food formulation according to the invention may also contain linoleic, α- and γ-linolenic acids, in amount sufficient to improve or maintain skin health. Suitable source of dietary linoleic acid may be sunflower or soybean oil.

EXAMPLES

The following examples are given by way of illustration only and in no way should be construed as limiting the subject matter of the present application. All percentages are given by weight unless otherwise indicated. The examples are preceded by a brief description of the figures.

Example 1

In vitro Anti-microbial Activity of Fatty Acids, Minimal Inhibitory Concentration (MIC) Determination A calorimetric method for quantitative measurement of the susceptibility of *Staphylococcus aureus, Staphylococcus intermedius* and *Malassezia pachydermatis* strains to fatty acids was developed. This method is based on the assays described by Hogan, J. S., et al, 1987, *J. Dairy, Sci.,* 70, 927-934 and Tiballi, R. N., et al., 1995, *J. Clin. Microbiol.,* 33 (4), 915-917.

The microorganisms used in this study were *Staphylococcus aureus* FSM 51, 52, 84 (food isolates), ATCC 6538, *Staphylococcus intermedius* BCCM™/LMG 9079, 13351 and *Malassezia pachidermatis* ATCC 14522. Staphylococcus strains were grown in Lab-Lemco broth (LL broth, Oxoid CM15) for 18-20 h at 30° C. and Malassezia was cultivated for 5 days at 30° C. in liquid Dixon medium (30 g Malt extract, 20 g Oxbile, 15 g Agar, 5 g Mycological peptone, 2.5 g Glycerol mono-oleate, 10 ml Tween™ 40, pH=5.4±0.2). After washing in saline (Oxoid, BR53), cell pellets were resuspended in LL broth supplemented with 0.15% agar (w/v).

Minimal inhibitory concentrations (MICs) of palmitoleic, lauric and oleic acids (NU-CHECK-PREP, Inc, DK, U-40-A, N-12-A, U-46-A respectively) were investigated in a microtiterplate assay using an oxidation-reduction dye, AlamarBlue™ (Interchim, Fr), as an indicator of growth. Each plate was set up with each of the test microorganisms as follows: one column, 110 µl of sterile LL broth supplemented with 0.15% agar (negative control), one column, 100 µl of sterile LL broth supplemented with 0.15% agar plus 10 µl of test microorganism (positive control), other columns, 100 µl of serial two fold dilutions of the test fatty acids (diluted in LL broth supplemented with 0.15% agar) plus 10 µl of microorganism (final concentration of $10^3$-$10^4$ cell/ml). Plates were incubated at 30° C. in ambient air and examined at 24 h and 4-5 days for *Staphylococcus* strains and *Malassezia* respectively. After incubation period, 25 µl of AlamarBlue™ solution (¼ diluted with 10 mM Phosphate Buffered Saline 0.05% Tween 20, Sigma P3563) were added to each well. After a second incubation of 2 h (*Staphylococcus*) and 1 day (*Malassezia*) at 30° C., endpoints were determined visually by observing a color change from blue (no growth) to pink (growth). MIC was defined as the lowest fatty acid concentration showing no growth (any color change).

TABLE 1

MIC ranges for four *S. aureus* strains, two *S. intermedius* strains and one *M. pachyderinatis* strain determined by a colorimetric method using AlamarBlue ™.

| | MIC range (mg/ml) | | |
|---|---|---|---|
| Fatty acid | *Staphylococcus aureus* | *Staphylococcus intermedius* | *Malassezia pachydermatis* |
| Oleic | >25 | >25 | >25 |
| Palmitoleic | 0.02 | 0.02-0.1 | 0.25->1 |
| Lauric | <0.2-0.4 | <0.2-0.8 | <0.2 |

Example 2

In-vivo Trials on the Effect of Dietary Fatty Acids on Epidermal Fatty Acids and Skin Barrier Function.

Material and Method

Animal Model

The in vivo animal model was the nude mouse fed diets enriched with various oil mixes at a constant level of total lipids. Nude mice were selected because of their lack of hair which allows easy access to skin for the measurement of biophysical parameters. Moreover, the composition of the major skin lipids is similar to that of humans, even though some differences in ceramide composition exist (Vicanova et al, *Arch. Dermatol. Res.*, 1999, 291: 405-412).

Protocol and Diets

Weanling nude mice (Iffa-Credo, L'Arbresle, France) were fed a standard irradiated diet for immuno-deficient mice (UAR, R03, UAR, Villemoisson, France) for four consecutive days. They were housed in a special area of the animal facility so as to maintain minimal exposure to potential pathogens. The room was maintained at a temperature of 26∓1° C. and a relative humidity of 45±5%. The mice were then allocated according to body weight into six experimental groups of eleven mice each. They were then provided ad libitum access to the experimental diets and to tap water for 35 days. These diets were based on a commercial diet for nude rodents (Kliba 2049, Kliba, Kaiseraugst, Switzerland) which was modified so as to provide 11% by weight of fat. All the fat content of these diets was provided under the form of fat mixes provided by Nestlé, which were added to the basal diet.

The source of the control diet was tallow. The other sources were formulated so as to contain variable amounts of linoleic acid, as well as other fatty acids of potential interest: α-linolenic acid, γ-linolenic acid, and fatty acids with known in vitro anti-microbial activity (lauric and paimitoleic acid). These diets were first irradiated. The sources and the fatty acid profile of the diet, as determined analytically after irradiation, is shown on Table 2.

TABLE 2

| Fat source Proportion | Ta. 100 | Ta./Su. 20/80 | Ta./Su. Ma. 20/ 20/60 | Ta./Su./ Flax 20/20/60 | Ta./Su. Co. 20/ 20/60 | Ta./Su. BCSO 20/20/60 |
|---|---|---|---|---|---|---|
| Protein | 23 | 23 | 23 | 23 | 23 | 23 |
| CHO | 46 | 46 | 46 | 46 | 46 | 46 |
| Fiber | 3.5 | 3.5 | 3.5 | 3.5 | 3.5 | 3.5 |
| Ash | 6 | 6 | 6 | 6 | 6 | 6 |
| Fat(a) | 11.3 | 11.2 | 11.2 | 11.1 | 10.6 | 10.9 |
| Fatty acids (% of total fatty acids, b) | | | | | | |
| Lauric | 0.5 | 0.2 | 0.2 | 0.2 | 23.5 | 0.4 |
| Myristic | 3.7 | 1.1 | 1.2 | 1.0 | 10.1 | 1.1 |
| Palmitoleic | 2.7 | 0.8 | 10.4 | 0.9 | 0.7 | 0.7 |
| Oleic | 33 | 32 | 46 | 27 | 19 | 22 |
| Linoleic | 5.4 | 38 | 16 | 23 | 16 | 37 |
| γ-linolenic | | | | | | 7.0 |
| α-linolenic | 0.5 | 0.5 | 0.5 | 23.6 | 0.8 | 5.8 |
| saturated | 51 | 24 | 22 | 22 | 61 | 22 |
| Total n-6 | 5.4 | 38.1 | 15.9 | 22.9 | 15.5 | 43.6 |
| Total n-3 | 0.5 | 0.5 | 0.5 | 23.6 | 0.8 | 5.8 |
| (n-6)/(n-3) | 10.8 | 82.8 | 30.5 | 1.0 | 19.4 | 7.6 |

Diet composition (g/100 g except for individual fatty acids: g/100 g fatty acids). Values are those supplied by the manufacturer, except (a): analyzed at NRC/QS and (b): analyzed by NRC/N. Ta.: tallow, Su.: sunflower, Ma.: macadamia, Co.: coconut.

These diets were fed for four weeks, at the end of which skin biophysical parameters were measured: pH, hydration, transepidermal water loss (TEWL). A dynamic test of skin barrier function regeneration after challenge was also tested. At the end of the 5 week-study period, mice were sacrificed and epidermal fatty acids were measured by gas chromatography.

Trans-epidermal Water Loss

Basal transepidermal water loss was measured after 30 days using the TEW A meter∩ 210 (from Courage & Khazaka) using the regular 6 mm probe.

Sample Collection

Mice were sacrificed 35 and 36 days after initiation of the trial. The skin was sampled in totality, except for the extremities and the head. The skin was applied dermis side down on a glass Petri dish containing about 3 ml of Trypsin-EDTA solution (Trypsin EDTA, 0.05% trypsin 0.53 mM EDTA 4 Na in HBSS, cat. 25300-054, GIBCO BRL Grand Island N.Y.). Skin samples were kept overnight at 4° C., and the dermis was manually scraped. The epidermis was frozen at −40° C., freeze-dried, and stored at −20° C. until analysis.

Analytical Methods

Epidermal lipids were extracted from about 100 mg of freeze-dried samples by a 2:1 chloroform/methanol solvent, rinsed by a 0.9% KCl solution, and fatty acids were determined after direct transesterification by HCl/methanol, using C23:0 as an internal standard.

Statistics

Except when specified, detection of group differences was carried out by ANOVA, and differences between groups were tested using Tukey's test. When only two groups were to be compared, a classical t-test was used. The level of significance was 0.05.

Results

Significant treatment effects were found on epidermal fatty acids, together with significant differences between groups (Table 3).

TABLE 3

| Fat source Proportion | Ta. 100 | Ta./Sun 20/80 | Ta./Su./Ma. 20/20/60 | Ta./Su. Flax 20/20/60 | Ta./Su./Co. 20/20/60 | Ta./Su./BCSO 20/20/60 |
|---|---|---|---|---|---|---|
| Linoleic acid | 9.8 ± 4.1 a | 24.7 ± 1.7 b | 13.6 ± 0.7 c | 17.8 ± 0.8 d | 15.4 ± 1.1 e | 25.1 ± 0.7 b |
| Palmitoleic acid | 5.7 ± 0.9 a | 3.2 ± 0.7 b | 5.8 ± 0.4 a | 3.3 ± 0.5 b | 5.46 ± 0.3 a | 2.8 ± 0.4 b |
| Lauric acid | <LD | <LD | <LD | <LD | 3.2 ± 1.3 | <LD |
| α-linolenic acid | <LD | <LD | <LD | 8.8 ± 0.8 a | 0.5 ± 0.2 b | 0.7 ± 0.1 b |
| γ-linolenic acid | <LD | <LD | <LD | <LD | <LD | 1.6 ± 0.1 |

Key epidermal fatty acids in nude mice fed diets enriched with various oil blends (% of fatty acids, mean ± SD, n = 10). Values sharing different letter superscripts are statistically significantly different at p = 0.05. <LD: lower than detection limit (corresponds to <0.1% and average <0.5%). Ta.: tallow, Su.: sunflower, Ma.: macadamia, Flax: flax seed, Co.: coconut.

Epidermal Anti-microbial Fatty Acid Composition

It was surprisingly found that palmitoleic acid concentration in the epidermis was dependent on dietary level and could be increased up to 6% of fatty acids (Table 3). Groups of mice fed tallow, coconut and macadamia oil (groups Tallow, Tallow/Sunflower/Coconut oil and Tallow/Sunflower/Macadamia) had the highest palmitoleic acid concentrations. The relationship between dietary and epidermal palmitoleic acid is illustrated in FIG. 1. It shows that in the absence of lauric acid, epidermal palmitoleic acid raises as a function of dietary content and seems to reach a plateau at about 4% of dietary fatty acids, which corresponds to 0.45% of diet in that case. An interaction with dietary lauric acid is evident however, since the Tallow/Sunflower/Coconut diet resulted in a concentration of palmitoleic acid of 5.5%, far higher than could be expected from its palmitoleic acid content only (outlier point in FIG. 1). This reveals that lauric acid can have a synergistic effect with palmitoleic acid, by boosting its concentration in the epidermis. This apparent synergistic effect of lauric acid on palmitoleic acid might be due either to the fact that lauric acid is a precursor of palmitoleic acid, or that it inhibits its degradation since it is one product of the degradation of palmitoleic acid by the β oxidation pathway.

Significant changes were also observed for epidermal lauric acid, as supplied by the tallow (20%) coconut oil (60%) sunflower oil (20%) mix, which increased from about detection level to 3.2% of epidermal fatty acids.

Therefore, the level of palmitoleic and lauric acids in the epidermis can be increased by dietary means. Both fatty acids are shown to be potent bactericides from in vitro experiments, e.g., against *staphylococcus aureus, staphylococcus intermedius*, and *malassezia pachydermatis*. Thus, there is a potential for an increased protection against the growth of opportunistic pathogens by the modulation of the bactericidal fatty acid composition of the epidermis or the sebum. There is a wide consensus that the most active fatty acids are C10:0 (capric), C12:0 (lauric), C14:0 (myristic), C16:1 (palmitoleic), C18:2 n-6 (linoleic), and C18:3n-3 (α-linolenic) (Puhvel et al, 1970; Kabara et al, 1972; Ko et al, 1978; Galbraith et al, 1971). Some fatty acids generally do not present significant bactericidal activity, and may even favor bacterial growth. This is the case for oleic acid.

Effect of Dietary Fatty Acids on Epidermal Linoleic Acid

It was found that the level of linoleic acid in the diet determined its level in the epidermis (Table 3), with a nearly 3-fold difference between the two extreme groups. This was observed over a range of intake that started from mouse requirements up to 6 times those. Internationally recognized requirements for linoleic acid are 1-2% of total dietary calories in humans, and 0.68% on a weight/weight basis in rats and mice (National Academy of Sciences. Recommended Dietary Allowances, 10th edition. National Academy of Sciences, Washington, 1989; National Research Council. Nutrient requirements of laboratory animals, 4th revised edition, Academy Press, Wash., 1995). Minimum AAFCO levels of linoleic acid in petfoods are 0.5% for cats and 1.0% for dogs, on a weight by weight basis.

Effect of Diet on Other Fatty Acids

The concentrations of α- and γ-linolenic acids could also be increased by dietary means, in that case by a factor of 10 at least (Table 3). While no pro-inflammatory challenge was included in that study, increasing the level of γ-linolenic acid could help reduce the manifestations of atopic eczema (Horrobin, D F., *Am. J. Clin. Nutr.* 2000; 71 (1 suppl.): 367S-372S), prostaglandin E2 production after delayed-type hypersensivity challenge (Wu D. et al, *Am. J. Clin. Nutr.* 1999; 70 (4): 536-543), and radiation-induced inflammation (Hopewell J W. et al, *Br. J. Cancer* 1993; 68 (1): 1-7), though γ-linolenic acid supplementation at 600 mg/day for 24 weeks did not improve hand dermatitis significantly in a human trial (Whitaker D K. et al, *Dermatology* 1996; 193 (2): 115-120). Another potential application for increasing epidermal γ-linolenic acid could be to inhibit 5α-reductase as shown for topical application (Liang T. et al, *J. Invest. Dermatol.* 1997; 109 (2): 152-157), thus allowing to reduce some manifestations of androgen-dependant skin disorders. However, efficacy in oral administration would need to be confirmed.

Biophysical Parameters

No statistically significant differences between treatments were also found for basal TEWL. This means that skin barrier function was maintained at an adequate level by all our fat mixes. This confirms that fat mixes containing appropriate levels of palmitoleic and lauric acids, as well as other fatty acids such as linoleic, α- and γ-linolenic acids can be formulated for addition into foods, especially foods for pets.

TABLE 4

| Fat Proportion | Ta. 100 | Ta./Su. 20/80 | Ta./Su./Ma 20/20/60 | Ta./Su./Fl 20/20/60 | Ta./Su./Co. 20/20/60 | Ta./Su./BCSO 20/20/60 |
|---|---|---|---|---|---|---|
| TEWL (basal) g/hm$^2$ | 13.0 ± 5.1 | 12.8 ± 3.0 | 11.4 ± 2.0 | 11.9 ± 3.6 | 11.1 ± 3.6 | 13.3 ± 4.8 |

Baseline values of the biophysical parameters in nude mice fed diets with various oil blends. Mean ± SD, with n = 11. Ta.: tallow, Su.: sunflower, Ma.: macadamia, Co.: coconut, Fl: Flax Example 3

Dry Dog Food

A feed mixture is made up of about 58% by weight of corn, about 5.5% by weight of corn gluten, about 22% by weight of chicken meal, 10% of a mix of dietary fatty acids consisting of 60% tallow, 25% sunflower oil, 15% coconut oil and salts, vitamins and minerals making up the remainder.

The feed mixture is fed into a preconditioner and moistened. The moistened feed is then fed into an extruder-cooker and gelatinized. The gelatinized matrix leaving the extruder is forced through a die and extruded. The extrudate is cut into pieces suitable for feeding to dogs, dried at about 110° C. for about 20 minutes, and cooled to form pellets.

It will be evident to those of skill in the art that part or totality of the fat mix, or of the fat and oils used, can be added at a later stage, e.g., as a coating.

This pet food thus provides a pet an amount of about 0.5% palmitoleic acid and about 0.01% dietary lauric acid, as well as about 1.8% of linoleic acid by weight of the final product. This dry dog food is found to help to maintain skin health and coat quality in dogs fed on a trial basis.

Example 4

A pet food is prepared as in example 3, except that the mix of dietary fatty acids consists of 40% beef tallow, 20% sunflower oil, 30% coconut oil and 10% flax. This pet food thus provides a pet an amount of about 1.3% dietary lauric acid and about 0.33% palmitoleic acid. The amount of linoleic acid is of about 1.5%. It further comprises a palatability enhancer suited to cats.

Cats receiving this formulation in a 12 week feeding trial exhibited noticeably shiner and overall improved skin and coat condition, when compared with a control group receiving a diet without the dietary fatty acid mix.

What is claimed is:

1. A pet food composition comprising a starch source, a protein source and at least a source of dietary lipids selected for their ability to modulate the content of anti-microbial fatty acids in the epidermis of mammals, wherein the source of dietary lipids is a mix of edible oils and fats or a food containing same, and comprises linoleic or linolenic acid in an amount of at least 1.0% by weight of the composition, dietary palmitoleic acid present in an amount of at least 2.5% to 10% by weight on a dry weight basis of total fatty acids and in an amount of at least 0.02% by weight of the pet food composition, and at least 1.0% of lauric acid by weight of the pet food composition, and in an amount sufficient to prevent or regulate growth of skin pathogens and microflora responsible for the generation of body surface or coat odors.

* * * * *